US00PP14161P29

(12) United States Plant Patent
Klemm

(10) Patent No.: US PP14,161 P2
(45) Date of Patent: Sep. 23, 2003

(54) GERANIUM PLANT NAMED 'KLEP01042'

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 10/259,969

(22) Filed: Sep. 29, 2002

(51) Int. Cl.[7] ..... A01H 5/00

(52) U.S. Cl. ..... Plt./332
(58) Field of Search ..... Plt./332

*Primary Examiner*—Kent Bell
(74) *Attorney, Agent, or Firm*—C. A. Whealy

(57) ABSTRACT

A new and distinct cultivar of Ivy Geranium plant named 'KLEP01042', characterized by its outwardly spreading and trailing plant habit; freely flowering habit; dark red-colored flowers arranged in hemispherical umbels held above and beyond the foliage on strong peduncles; and tolerance to high temperatures.

1 Drawing Sheet

Botanical classification/cultivar designation: *Pelargonium peltatum* cultivar 'KLEP01042'.

BACKGROUND OF THE INVENTION

The present invention relates to a new and distinct cultivar of Ivy Geranium plant, botanically known as *Pelargonium peltatum*, and hereinafter referred to by the name 'KLEP01042'.

The new Ivy Geranium is a product of a planned breeding program conducted by the Inventor in Stuttgart, Germany. The objective of the breeding program was to develop new Ivy Geraniums with uniform plant habit and interesting flower and foliage colors.

The new Ivy Geranium originated from a cross-pollination made by the Inventor in 1997 of a proprietary selection of *Pelargonium peltatum* identified as code number PL 707, not patented, as the female, or seed, parent with the *Pelargonium peltatum* cultivar 'Kleblue', disclosed in U.S. Plant patent applciation Ser. No. 09/250,014 (now abandoned), as the male, or pollen, parent. The cultivar KLEP01042 was discovered and selected by the Inventor as a flowering plant within the progeny from this cross-pollination in a controlled environment in Stuttgart, Germany, in June, 1998.

Asexual reproduction of the new cultivar by terminal cuttings taken in a controlled environment in Stuttgart, Germany since 1999 has shown that the unique features of this new Ivy Geranium are stable and reproduced true to type in successive generations of asexual reproduction.

SUMMARY OF THE INVENTION

The following traits have been repeatedly observed and are determined to be the unique characteristics of 'KLEP01042'. These characteristics in combination distinguish 'KLEP01042' as a new cultivar and distinguish it from other known Ivy Geranium cultivars:

1. Outwardly spreading and trailing plant habit.
2. Freely flowering habit.
3. Dark red-colored flowers arranged in hemispherical umbels held above and beyond the foliage on strong peduncles.
4. Tolerant to high temperatures.

Plants of the new Ivy Geranium are not as vigorous, but have darker red-colored flowers than plants of the female parent, the selection PL 707. Plants of the new Ivy Geranium differ primarily from plants of the male parent, the cultivar Kleblue, in flower color as plants of the cultivar Kleblue have purple-colored flowers.

The new Ivy Geranium can be compared to plants of the cultivar 'Kleored', not patented. However, in side-by-side comparisons conducted in Stuttgart, Germany, plants of the new Ivy Geranium differed from plants of the cultivar Kleored in the following characteristics:

1. Plants of the new Ivy Geranium had glossier leaves than plants of the cultivar Kleored.
2. Plants of the new Ivy Geranium had darker red-colored flowers than plants of the cultivar Kleored.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Ivy Geranium. The photograph comprises a side perspective view of a typical flowering plant of 'KLEP01042' grown in a 12-cm container.

DETAILED BOTANICAL DESCRIPTION

Plants of the cultivar KLEP01042 have not been observed under all possible environmental conditions. The phenotype may vary somewhat with variations in environment, such as temperature and light intensity, without, however, any variance in genotype.

The aforementioned photograph and following observations and measurements describe plants that were planted in January in 12-cm pots in Stuttgart, Germany, and grown under commercial practice in a glass-covered greenhouse with day temperatures ranging from 18 to 22° C., night temperatures ranging from 14 to 16° C., and light levels ranging from 20,000 to 55,000 lux. Plants were pinched one time. The photograph and information for the detailed botanical description were taken in May, or about 3.5 months after planting rooted young plants.

In the following description, color references are made to The Royal Horticultural Society Colour Chart, 1995 Edition, except where general terms of ordinary dictionary significance are used.

Botanical classification: *Pelargonium peltatum* cultivar KLEP01042.

Parentage:

*Female parent.*—Proprietary selection of *Pelargonium peltatum* identified as code number PL 707, not patented.

*Male parent.*—*Pelargonium peltatum* cultivar Kleblue, disclosed in U.S. Plant patent application Ser. No. 09/250,014 (now abandoned).

PROPAGATION:

*Type cutting.*—Terminal cuttings.

*Time to initiate roots.*—Summer: About 10 days at 22° C. Winter: About 12 days at 18 to 20° C.

*Time to produce a rooted young plant.*—Summer: About 16 days at 22° C. Winter: About 18 days at 18 to 20° C.

*Root description.*—Fine; white in color.

*Rooting habit.*—Dense.

Plant description:

*General appearance.*—Outwardly spreading and trailing plant habit; mounded; densely foliated.

*Growth and branching habit.*—Moderately vigorous. Freely branching, about three or four lateral branches develop.

*Plant height* (*to top of flower umbels*).—About 22 to 26 cm.

*Plant height* (*to top of foliar plane*).—About 14 to 17 cm.

*Plant width.*—About 18 to 20 cm.

*Lateral branches.*—Length: About 5 to 6 cm. Internode length: About 2.5 to 3 cm. Texture: Pubescent; rough. Color: 137D.

*Foliage description.*—Arrangement: Alternate, simple. Length: About 4 to 5 cm. Width: About 8 cm. Shape: Reniform. Apex: Rounded. Base: Lobed, slightly overlapping. Margin: Entire with shallow lobes. Venation pattern: Palmate. Texture, upper and lower surfaces: Glabrous; leathery. Color: Young and fully expanded foliage, upper surface: 137A. Young and fully expanded foliage, lower surface: 137D. Venation, upper and lower surfaces: 137A. Zonation: Width: About 6 to 10 mm. Color: 200A. Petiole: Length: About 4 to 5 cm. Diameter: About 3 to 4 mm. Color, upper and lower surfaces: 137D.

Flower description:

*Flower arrangement.*—Dark red-colored flowers arranged in rounded hemispherical umbels arising from apical leaf axils. Umbels displayed above and beyond the foliage on strong peduncles. Flowers double in form, rounded and cup-shaped. Umbels persistent, flowers not persistent. Flowers not fragrant.

*Quantity of flowers.*—Freely flowering habit; at full flower, plants have at least about 6 to 8 open and developing umbels with about 10 to 15 flowers and flower buds per umbel.

*Flowering season.*—Year-round under greenhouse conditions. In the garden, flowering is continuous from spring until fall.

*Time to flower.*—Early flowering; plants start flowering about 90 days after planting rooted young plants.

*Flower longevity.*—Flowers last about 5 to 10 days on the plant.

*Umbel size.*—Height: About 8 to 10 cm. Diameter: About 8 to 10 cm.

*Flower size.*—Diameter: About 5 cm. Depth (height): About 1.5 cm.

*Flower buds.*—Length: About 1 cm. Diameter: About 6 to 8 mm. Shape: Elliptical. Color: 138A.

*Petals.*—Quantity per flower: About 10 to 12. Length: About 2.2 cm. Width: About 1.5 cm. Shape: Ovate. Apex: Rounded. Base: Attenuate. Margin: Entire. Texture, upper and lower surfaces: Smooth, velvety. Color: When opening, upper surface: 59A. When opening, lower surface: 64B. Fully opened, upper surface: 53A, towards base, 67B; color does not fade with subsequent development. Fully opened, lower surface: 64B, towards base, 67D. Venation, upper surface: 53A. Venation, lower surface: 53C.

*Petaloids.*—Quantity per flower: None to about five. Length: About 3 to 10 mm; irregular in size. Width: About 1 to 5 mm; irregular in size. Shape: Variable, irregular. Apex: Mostly rounded. Base: Attenuate. Margin: Mostly entire. Texture, upper and lower surfaces: Smooth, velvety. Color: When opening, upper surface: 67A. When opening, lower surface: 67D. Fully opened, upper surface: 67B, towards base, 67C; color becoming closer to 67A with development. Fully opened, lower surface: 67D. Venation, upper surface: 67A. Venation, lower surface: 67B.

*Sepals.*—Quantity per flower: Five, arranged in a single whorl. Length: About 8 to 10 mm. Width: About 4 to 6 mm. Shape: Elliptical. Apex: Acute. Margin: Entire. Texture, upper and lower surfaces: Pubescent, velvety. Color, upper and lower surfaces: 138A.

*Peduncle* (*umbel stem*).—Length: About 10 to 14 cm. Diameter: About 4 mm. Angle: Erect. Strength: Strong. Texture: Pubescent; rough. Color: 138A.

*Pedicel* (*individual flower stem*).—Length: About 1.8 to 2.2 cm. Diameter: About 1.5 mm. Angle: Erect. Strength: Moderately strong. Texture: Pubescent; rough. Color: 137C.

*Reproductive organs.*—Androecium: Anther quantity per flower: Five. Anther length: About 3 mm. Anther shape: Ovate. Anther color: 64A. Pollen amount: Moderate. Pollen color: 33B. Gynoecium: Pistil quantity per flower: One. Pistil length: About 8 to 12 mm. Stigma shape: Five-parted, star-shaped. Stigma color: 57C. Style length: About 3 to 5 mm. Style color: 57D. Ovary color: 149D.

*Seed.*—Length: About 3 to 6 mm. Diameter: About 1.5 to 2 mm. Shape: Ovoid. Color: Brownish.

Disease/pest resistance: Plants of the new Ivy Geranium have not been observed to be resistant to pathogens and pests common to Ivy Geraniums.

Weather tolerance: Plants of the new Ivy Geranium have been observed to tolerate rain, wind, and temperatures from about 8 to 34° C.

It is claimed:

1. A new and distinct cultivar of Ivy Geranium plant named 'KLEP01042', as herein illustrated and described.

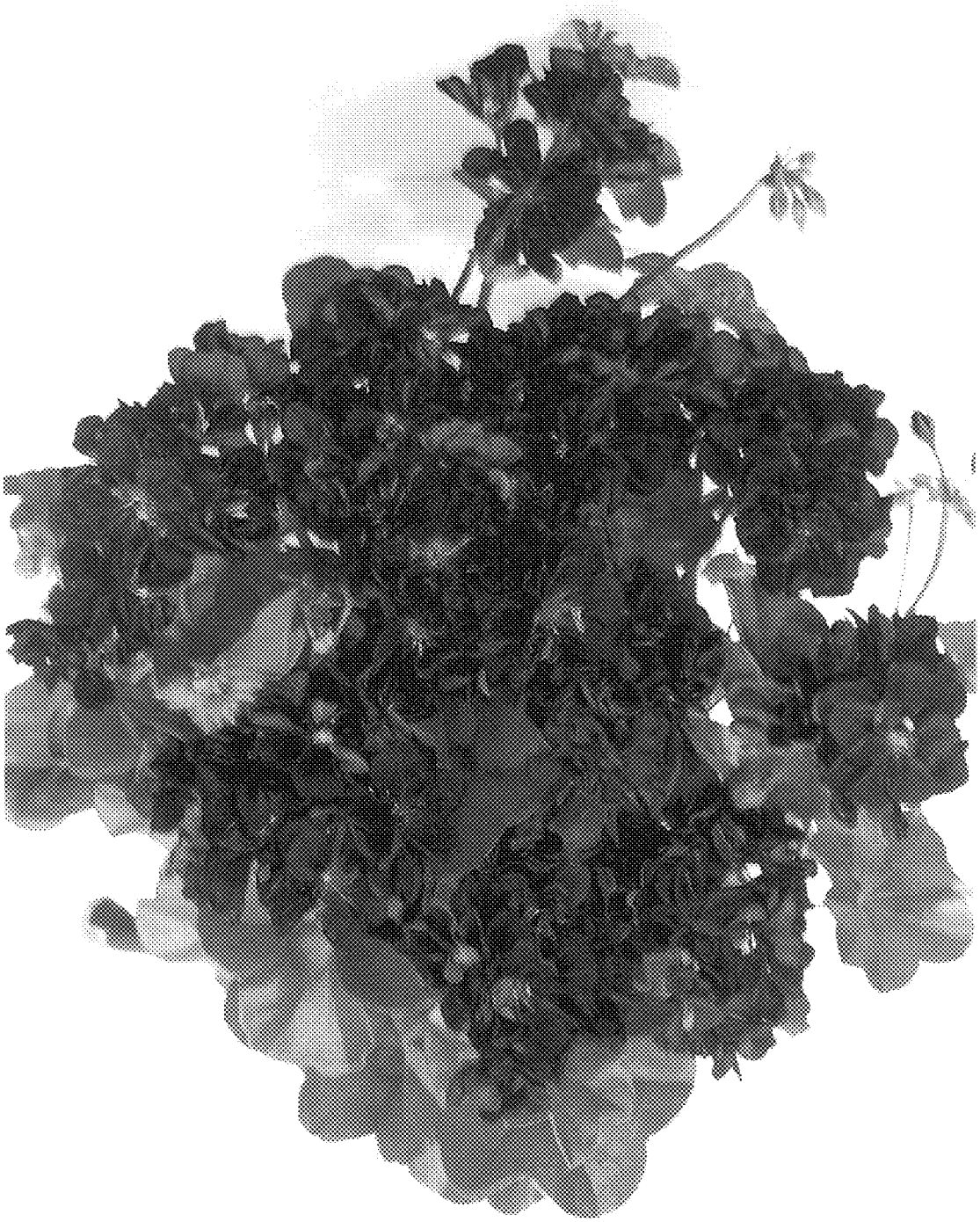

* * * * *